Figure 1A:
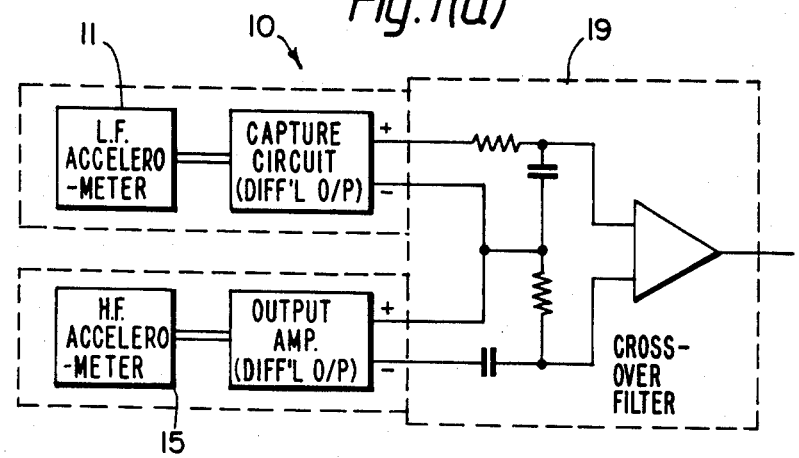

United States Patent
Brown et al.

[11] Patent Number: 4,611,491
[45] Date of Patent: Sep. 16, 1986

[54] ACCELEROMETER SYSTEM

[75] Inventors: Kenneth R. Brown, Kirknewton; Norman F. Watson, South Queensferry, both of Scotland

[73] Assignee: Ferranti plc, England

[21] Appl. No.: 724,923

[22] Filed: Apr. 19, 1985

[30] Foreign Application Priority Data

May 5, 1984 [GB] United Kingdom ............ 84 11578

[51] Int. Cl.$^4$ ............................................. G01P 15/08
[52] U.S. Cl. .................................. 73/517 B; 73/510; 73/654
[58] Field of Search .................. 73/517 B, 510, 518, 73/519, 520, 654, 35

[56] References Cited

U.S. PATENT DOCUMENTS 4,337,641  7/1982  Sugihara et al. ...................... 73/35

Primary Examiner—Anthony V. Ciarlante
Attorney, Agent, or Firm—Kerkam, Stowell, Kondracki & Clarke

[57] ABSTRACT

An accelerometer system (FIG. 2) suitable for measuring low-frequency accelerations in inertial systems is also able to measure high-frequency vibrational accelerations which give rise to e.g. sculling effects in inertial platform arrangements employing three such accelerometer systems. The system comprises a low-frequency inertial quality force feedback accelerometer 10' and a high-frequency, e.g. piezo-electric, accelerometer 46. The output of h.f. accelerometer 46 is summed at 48 with the feedback signal from transducer 32' in the l.f. accelerometer feedback loop, the faster response of the h.f. accelerometer providing most of the feedback to balance the l.f. loop without significant displacement of mass 11'. Up to several hundred Hz the displacement of mass 11' and the feedback component from transducer 32' is only to overcome the error in the h.f. accelerometer signals and at higher frequencies the response of the h.f. accelerometer alone provides a measure of acceleration offering a wide system bandwidth. Because of the limited displacement of the proof mass the l.f. feedback loop may have a transfer function minimizing vibropendulous errors at lower frequencies.

10 Claims, 6 Drawing Figures

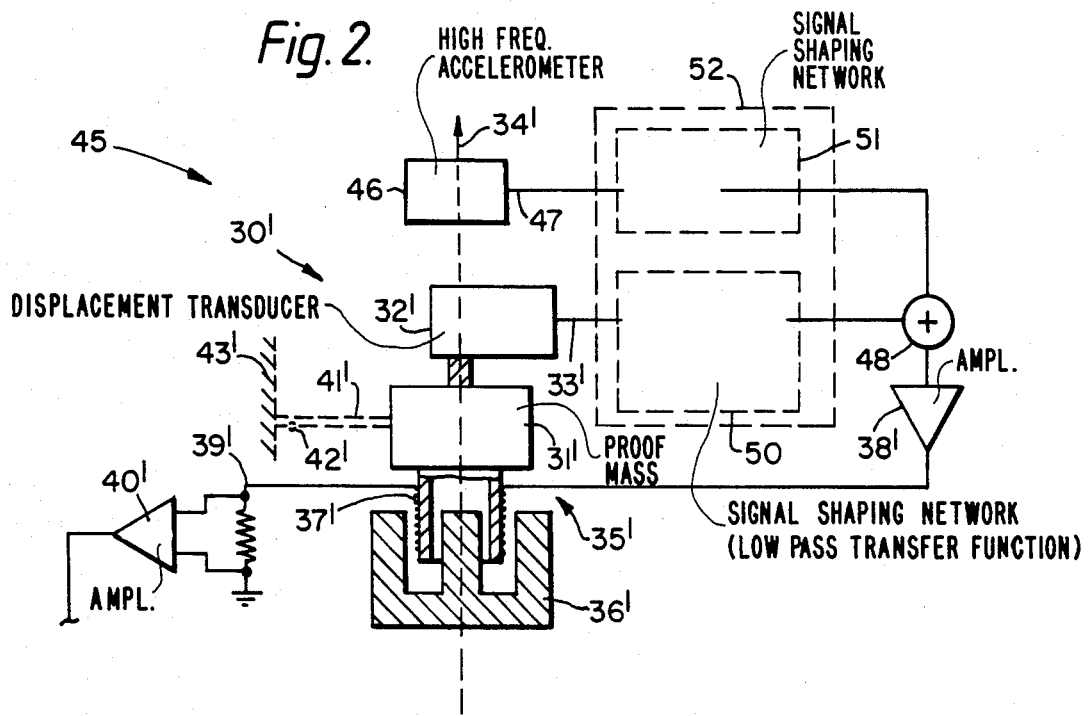
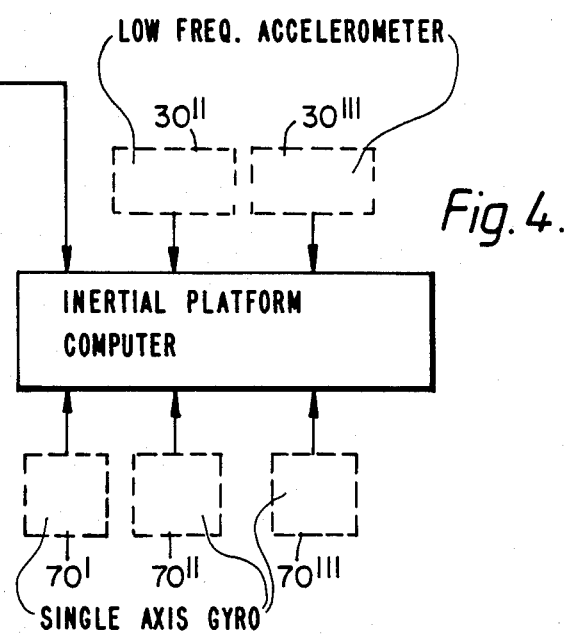

ACCELEROMETER SYSTEM

This invention relates to accelerometer systems, particularly of the type employed in inertial platforms.

Inertial platform arrangements are well known employing a plurality of gyroscopes and accelerometers arranged to monitor linear and rotational motion of the platform. The accelerometers employed to sense motion of the platform are required to measure accurately zero acceleration, unidirectional acceleration and low-frequency vibrational acceleration of the platform consistent with motion of a vehicle carrying it that is, inertial acceleration. Whilst an inertial quality accelerometers will be 'low-frequency' types it will be appreciated that all frequency accelerometers need not be of inertial quality. In this specification it is assumed that 'low-frequency' and 'inertial quality' are synonynous for inertial quality accelerometers having a typical operating bandwidth from zero to several hundred hertz.

Within an inertial platform construction there are several sources of error due both to imperfections of components and due to external forces, particularly what are referred to in this specification as high-frequency vibrations, that is, vibrations at frequencies above the normal operating range of the inertial quality accelerometers.

Such sources of error and the inducing motions are discussed in the text books, for instance by N. Fernandez and G. R. Macomber in 'Inertial Guidance Engineering' published by Prentice-Hall Inc., Englewood Cliffs, N.J., U.S.A. One effect, sculling motion, is of particular interest in that high-frequency linear and rotational vibrations about two orthogonal axes result in a non vibrational displacement component about a third orthogonal axis, such component being within the operating bandwidth of the low-frequency inertial quality accelerometer.

With the commonly employed gimbal-mounted gyro systems vibrational errors tend to be small and give rise to effects which are readily eliminated. However in strapdown systems in which the platform and its components are rigidly fixed with respect to a carrying vehicle the levels of such vibrational motions are higher and unavoidable. This is particularly true of the more recently developed mechanically dithered laser gyro systems.

To mitigate the effects of such high-frequency vibrations on the low-frequency accelerometers it becomes necessary to measure those high-frequency vibrational accelerations along the three orthogonal axes of the inertial quality accelerometer and derive therefrom correction to be applied to the low-frequency accelerations measured.

It is apparent that this may be achieved in a number of ways. Firstly, each low-frequency inertial quality accelerometer may be constructed with an operating bandwidth extending to higher frequencies in excess of one kilohertz, but such a device is complex and essentially expensive to produce whilst compromising on accuracy and/or reliability at the extremes of operating range which are by definition of most interest.

Secondly, in addition to the inertial quality accelerometers employed at low-frequencies, high-frequency accelerometers, that is, with an operating range of tens of hertz to several kilohertz, may be employed solely to detect vibrational movements within the system. Signals produced by the high-frequency accelerometers are processed by application of suitable algorithms to provide corrections to the signals produced by the low-frequency accelerometers.

The use of separate high- and low-frequency accelerometers does lead to other potential sources of error. The magnitudes of signals produced by all six accelerometers vary from device to device and the correction algorithm has to be tailored as a function of the accelerometers' characteristics. If any of the accelerometers are changed or their characteristics vary then scale factor errors are introduced requiring the whole system to be re-calibrated.

A form of accelerometer system designed to mitigate these effects is described in our co-pending application No. 82.24855 publication number 2146775 and shown schematically in FIG. 1(a) hereof.

The system consists essentially of a low frequency inertial quality accelerometer 10 and a high frequency accelerometer 15 the outputs of the two acceleometers being combined by way of a cross-over filter network 19 giving a unitary output in response to accelerations in a wide bandwidth extending from unidirectional inertial accelerations to high-frequency vibrational accelerations. The accelerometers are scaled as to output signal amplitudes and the network components chosen to give a substantially uniform response over the extended bandwidth.

The cross-over frequency may be chosen at will within the operating bandwidths of both accelerometers but is expected to be chosen in a frequency band at which neither is expected to function in practice, thereby minimising the effects of any non-linearities caused by the combining of signals. For example, the low frequency accelerometer will normally be expected to register inertial accelerations below a few tens of hertz and the high frequency accelerometer to register vibrational accelerations above a few hundreds of hertz, thereby making it convenient to have a cross-over frequency of say 30–50 hertz.

It must be borne in mind that the accuracy offered by the high frequency accelerometer is lower than that of the inertial quality accelerometer and also that any significant mis-matching of signals and any scaling errors resulting therefrom (however minimal) begin at a lower frequency than might be expected from the inertial quality (low frequency) alone which as stated is accurate to several hundred hertz.

However, merely raising the cross-over frequency does not necessarily increase the frequency range at which output accuracy is assured.

A common constructional form of inertial quality accelerometer is the force feedback accelerometer in which displacement of an inertial, or proof, mass by an acceleration force is sensed and causes generation of a capture current in an electromagnetic coil to balance the force, said current being a measure of the acceleration. Such a force feedback accelerometer is often constructed as a pendulous accelerometer, the proof mass being supported and constrained to pivotal motion about an axis by jewelled gimbals or a hinged beam. The Ferranti model FA2 is an example of the latter form of construction. All such inertial quality accelerometers are subject to vibropendulous errors (as described in the aforementioned book) when the feedback loop requires measurable displacement of the inertial mass to generate a capture or restoring current. One form of construction proposed in U.K. Pat. No. 830,076 is intended to remove the effect of vibropendulosity by eliminating displacement of the pendulous inertial mass through the use of an auxiliary accelerometer. The auxiliary accelerometer responds to the same acceleration forces as the inertial mass and provides a signal for the feedback loop, developing an inertial mass restoring torque without the necessity for the pendulous inertial mass itself to be fully displaced.

The elimination of sources of error characteristic of the constructional nature of an inertial quality accelerometer does not of itself however effect the operating bandwidth of what is a low frequency accelerometer.

It is an object of the present invention to provide a wide bandwidth single axis accelerometer system including a force feedback inertial quality accelerometer, such as a pendulous type, which mitigates disadvantage outlined above associated with known systems and instruments.

It is also an object of the present invention to provide an inertial platform arrangement including a triaxial combination of such single axis accelerometer systems.

According to a first aspect of the present invention a single axis accelerometer system comprises
(i) a low frequency accelerometer (as herein defined) of the force feedback type including an inertial proof mass mounted to be displaced from a datum position along a sensitive axis by an acceleration force, a displacement transducer operable to produce a feedback signal as a function of displacement of the proof mass from the datum position and capture means responsive to a capture current flowing therein to produce a restoring force on the proof mass to balance the acceleration force, said capture current being provided as a function of the feedback signal,
(ii) A high frequency accelerometer (as herein defined) fixed in relation to the low frequency accelerometer and responsive to high frequency vibrations along said sensitive axis to produce an acceleration related signal, and
(iii) signal processing means operable to mix the feedback signal from the proof mass displacement transducer and the acceleration related signal produced by the high frequency accelerometer and derive therefrom the capture current.

According to a second aspect of the present invention an inertial platform arrangement includes three single-axis accelerometer systems as defined in the preceding paragraph arranged with their sensitive axes mutually orthogonal.

Figure 1B:
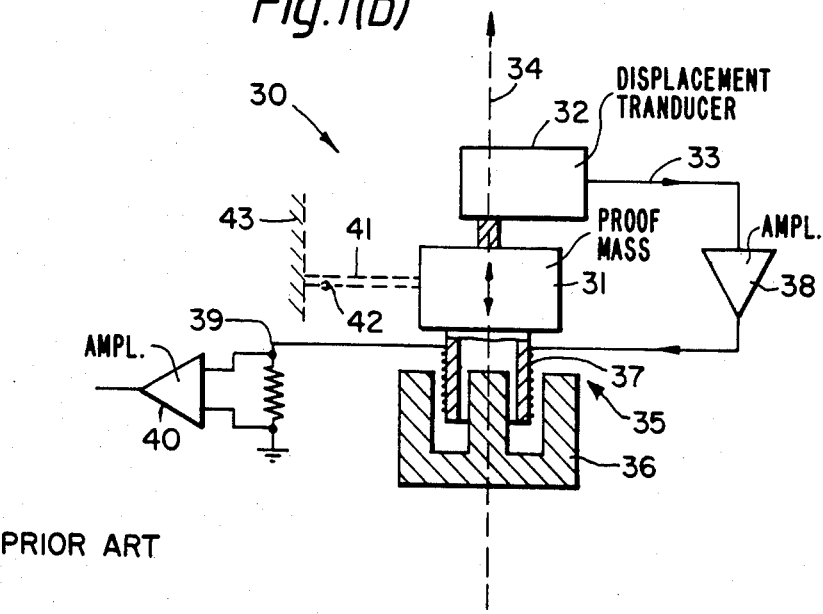
Figure 3:
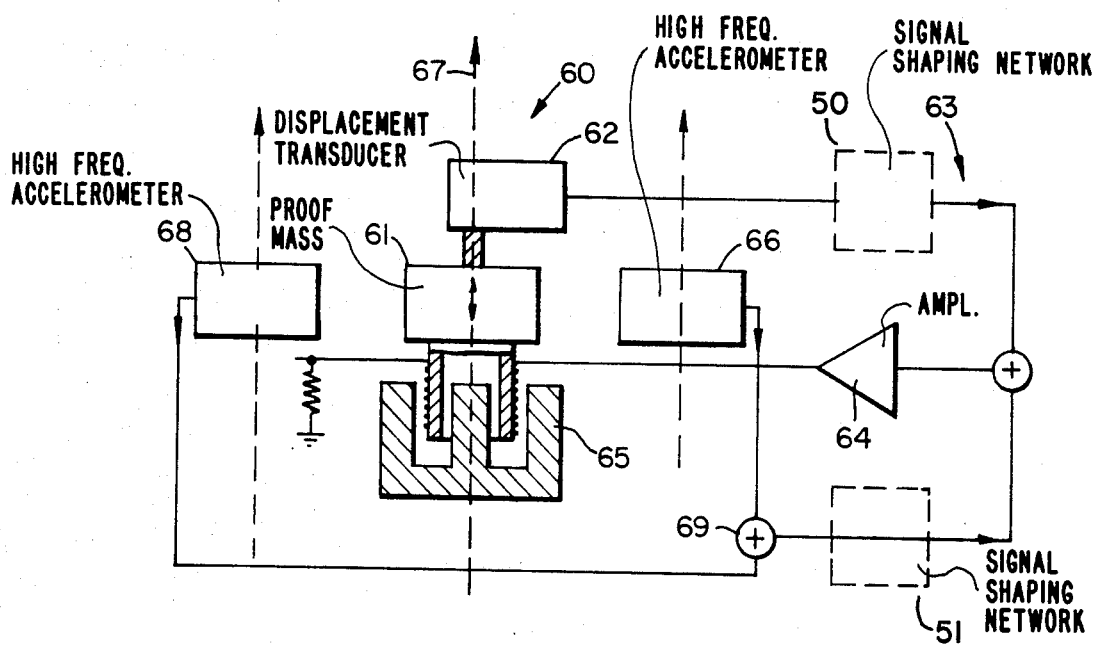
Figure 5:
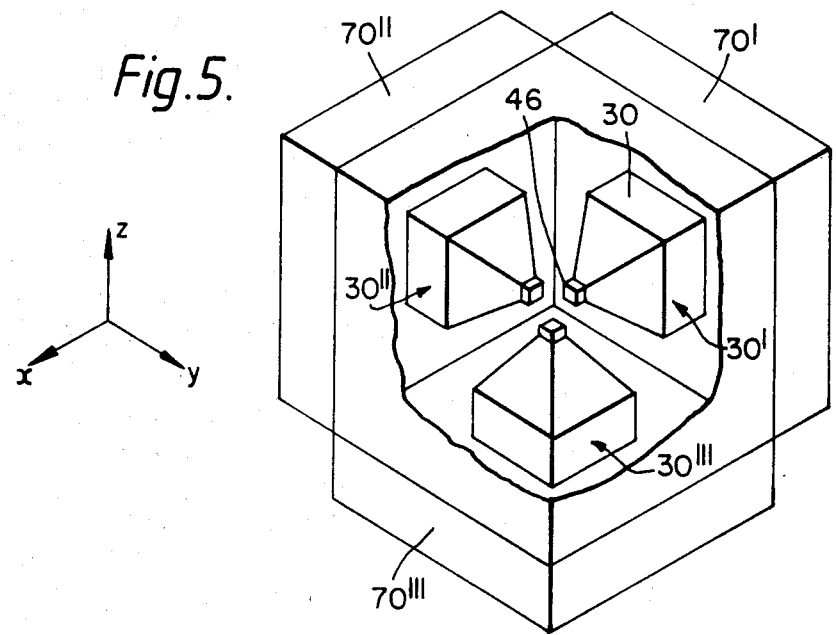

Embodiments of the invention will now be described by way of example with reference to the accompanying drawings, in which:

FIG. 1(a) is a schematic representation of an single axis wide band accelerometer system described in the aforementioned co-pending application, FIG. 1(b) is a schematic electro-mechanical circuit diagram of a known inertial quality single axis force feedback pendulous accelerometer, FIG. 2 is a schematic electro-mechanical circuit diagram of a single axis accelerometer system according to the present invention incorporating a force feedback pendulous accelerometer of the type shown in FIG. 1(b) and a single high frequency accelerometer, FIG. 3 is a block schematic diagram of a single axis accelerometer system according to the present invention incorporating a force feedback pendulous accelerometer of the type shown in FIG. 1(b) and a pair of high frequency accelerometers disposed about the centre of percussion of the force feedback accelerometer, FIG. 4 is a schematic block diagram of the measuring and signal processing elements including the accelerometer system of FIG. 2 associated with an inertial platform, and FIG. 5 is a schematic perspective view of a strap-down inertial platform including a laser gyro arrangement and three accelerometer systems of the form of FIG. 2 showing the disposition of individual accelerometers.

Referring to FIG. 1(b) a low frequency inertial quality accelerometer is shown by the pendulous force feedback instrument 30. A suitable instrument is the Ferranti type FA2. It comprises an inertial, or proof, mass 31 having attached thereto a displacement transducer 32 operable to produce a feedback signal on output line 33 the magnitude of which signal is a function of the displacement of the body 31 from a datum position along a sensitive axis 34 of the accelerometer. The transducer comprises an electromagnetic pick-off coupled to an amplifier providing an output voltage the magnitude of which is directly proportional to the magnitude of the proof mass displacement.

Capture means 35 comprises a magnet arrangement 36 providing a field in which is disposed an electromagnetic driving coil 37 carried by the proof mass 31, the passage of an electric current, hereinafter referred to as the capture current, through the coil exerting a force on the proof mass along the sensitive axis 34.

The capture current is derived from the feedback voltage on line 37 by a transconductance amplifier 38 and the direction of current flow in the coil is such that the resultant force exerted on the proof mass is in opposition to an acceleration force causing displacement of the mass, said coil 'capturing' the mass after it has been displaced through a distance at which the feedback signal, and the restoring force generated thereby, balances the displacement force due to acceleration. The balanced acceleration force is measured in terms of the capture current flowing in the coil 37 at output 39, for example by an amplifier 40 giving a single or differential output (as shown at 13, 14 in FIG. 1(a)).

The proof mass 31 is supported at its datum position by a cantilever arm 41 including a hinge 42 about which the arm is constrained to pivot with respect to the body, indicated at 43, of the accelerometer. The displacement along axis 34 is normally small and may be considered substantially rectilinear even though the proof mass is pivoted about hinge 42. The construction form is an example of a pendulous accelerometer commonly employed in inertial quality accelerometers, although the proof mass 31 may be supported at its datum position and in respect of displacement therefrom by other known forms of suspension which it is, not necessary to describe.

As stated, the pendulous accelerometer is limited in bandwidth at the higher frequencies by mechanical responsiveness of the accelerometer including the requirement to physically displace the proof mass in order to establish a capture current although the use of a closed feedback loop enables the gain and transfer function to be controlled to enable a substantially linear response up to several hundred hertz vibrational acceleration. However such tailoring of the feedback loop to effect phase advance of the feedback signal effectively increases suspension compliance and increases the susceptibility of the pendulous accelerometer to the so-called vibropendulous errors when subjected to vibration at lower frequencies, such vibropendulous errors also being a function of the magnitude of proof mass displacement.

A single axis accelerometer in accordance with the present invention is shown at 45 in FIG. 2. The accelerometer system includes an inertial qualitity low frequency force feedback pendulous accelerometer 30' corresponding to the device 30 of FIG. 1(b) and like parts are given like, but primed, reference numerals.

In addition to the low frequency accelerometer 30' it comprises an auxiliary accelerometer in the form of a high frequency vibration measuring accelerometer 46, such as a miniature piezo electric type 2250A manufactured by Endevco Corp., San Juan Capistrano, Calif., U.S.A., operable to measure accelerations along a sensitive axis in the range of tens of hertz to the tens of thousands of hertz. The high frequency accelerometer is located in relation to the housing 43' of the low frequency accelerometer with its sensitive axis coaxial, or at least parallel, with that of the low frequency accelerometer, that is, along axis 34'.

The accelerometer 46 produces an alternating voltage of amplitude proportional to the virational acceleration amplitude on line 47. The output line 47 is connected to a summing junction 48 with the line 33' from the displacement means, the acceleration related output of the high frequency accelerometer being summed with the displacement-related feedback signal applied to a transconductance amplifier 38'. The amplitude of the signal from the high frequency accelerometer is controlled in relation to the gain of the feedback loop so that the signal produced thereby in response to an acceleration force is substantially equal to that generated by the displacement transducer 32' of the low frequency accelerometer.

In operation an acceleration force acting along the sensitive axis 34' influences both the proof means 31' and the piezo-electric element (not shown) of the high frequency accelerometer 46. Because the proof mass displacement is effectively an integration of the acceleration force acting there is an inevitable lag compared with the response of the high frequency accelerometer and the acceleration related signal thereof which applied to amplifier 38' causes a capture current to flow in coil 37' of substantially the same magnitude as that which would eventually be generated by displacement of the proof means. However, the capture current flows and the proof mass is captured before significant displacement of the proof mass occurs.

The high frequency accelerometer 46 although small and responsive does not have the accuracy required for inertial applications, being no better than of the order of one or two percent and so proof mass 31' still undergoes some displacement. This is measured by transducer 32' and applied to the amplifier 38' in addition to the signal from accelerometer 46, the signal and the proof mass displacement necessary to cause it being only at the level of the error in the high frequency accelerometer response rather than at the level of the acceleration acting.

At low frequencies of a few hertz or for unidirectional accelerations the high frequency accelerometer 46 does not respond and in the most critical area of operational accuracy measuring inertial accelerations the low frequency accelerometer 30' effectively functions alone in known manner. Because the low frequency accelerometer is now required only to measure very low frequency accelerations and provide only a correction for the inaccuracy of the high frequency accelerometer at other frequencies, the feedback loop may be configured to provide low suspension compliance with high gain to minimise proof mass displacement, thereby minimising vibropendulous errors.

At higher frequencies the high frequency accelerometer with its earlier response effectively causes generation of the capture current to the accuracy of the high frequency accelerometer, which may be over 90%, and the low frequency accelerometer closed loop provides the remaining source of capture current bring the accuracy towards the near 100% accuracy expected of inertial quality instruments while requiring to effect only small mass displacements.

At even higher frequencies of the order of hundreds of hertz, the suspension compliance of the low frequency accelerometer (which is tailored for low frequency performance) causes its response to deteriorate and the feedback signal it provides to fall off to zero. The capture current is still generated and the acceleration output signal is provided on the basis of the high frequency accelerometer output only. The high frequency accelerometer continues to respond up to frequencies of several kilohertz so that the accelerometer system accuracy falls from the near 100% mark towards that of the high frequency accelerometer alone.

It will be appreciated that the accelerometer system provides maximum accuracy below the cut-off frequency of the low frequency accelerometer and above that, an accuracy as good as is available from any high frequency accelerometer. Apart from the summing junction 48 combination of signals within the feedback loop requires fewer components than combining acceleration signals in the arrangement of FIG. 1(a), and requires less consideration to component matching.

For instance in the system of FIG. 1(a) component falut or mis-match in the cross-over circuit could lead to a non-linearity in response which is best avoided by keeping the cross-over frequency reatively low between frequency bands of interest. However, any mis-match between accelerometer output levels (particularly the high frequency accelerometer as this is less well controlled) will also cause a discontinuity at the cross-over frequency and an error extending over a greater part of the response spectrum.

With the system described with reference to FIG. 2 it will be seen that the only discontinuity that can occur results from a mis-match of the high frequency accelerometer output but that any deviation at lower frequencies is masked by the feedback loop and system output due solely to this accelerometer is confined to a smaller part of the spectrum.

Furthermore it can be reiterated that while the upper response is extended with reasonable accuracy by the high frequency accelerometer the low frequency accelerometer can be specifically configured to remove low frequency error sources, such as the vibropendulosity described above.

In a basic arrangement described in FIG. 2 the signals from the high frequency accelerometer 46 and displacement transducer 32' are combined by simply summing them. It will be appreciated that either or both signals may be modified by signal shaping networks indicated in outline at 50 and 51 in signal shaping means 52. The forms of signal modification in acceleration responsive signals are well known and do not require comprehensive or detailed discussion.

Signal shaping network 50 may modify the feedback signals from displacement transducer 32', which may produce a rectified alternating pick-off signal, with, say, a low pass transfer function to remove any high frequency alternating components and which, by virtue of an integrating term, increases the loop gain at low or zero frequencies.

Signal shaping network 51 may act, not so much to modify the signals by a transfer function as to limit the signal bandwidth. For instance some piezo electric accelerometers use a capacitive transducer and have a d.c. offset on which an a.c. acceleration signal is superimposed, and the network 51 may include a capacitor for d.c. blocking. Also the accelerometer produces an a.c. output in response to frequencies greater than 10 kilohertz and possibly up to 50 kilohertz. Whilst the passage of an alternating current at such frequencies through the coil and outside of the feedback loop response bandwidth should be "invisible" it is possible for the coil to exert a rectifying effect on the alternating current and introduce a direct current which registers as an acceleration error. In a situation as outlined hereinbefore in relation to inertial platforms in which the high frequency acceleration signals are combined with ones on other axes digitally the acceleration signals are sampled and the high frequency accelerometer does not require a response bandwidth extending significantly above 3 kilohertz; to avoid any risk of errors due to higher frequency signals the network 51 may also include a low-pass filter to limit the signal bandwidth as required.

It will be appreciated that the sensitive axes of the high frequency accelerometer 46 and the low frequency accelerometer must be aligned to respond to the same linear acceleration forces. Ideally the centres of percussion of the two instruments should be coincident but given that the high frequency accelerometer is located adjacent the low frequency accelerometer it is located with the directions of their sensitive axes at least parallel if not coincident as shown in FIG. 2.

An alternative arrangement is shown schematically in FIG. 3. A low frequency force feedback accelerometer 60 comprises a displaceable proof mass 61, displacement transducer 62, feedback loop 63 including transconductance amplifier 64 and capture means 65 including an electromagnetic coil mechanically coupled to the mass 61 and receiving current from the amplifier 64. A first high frequency accelerometer 66 is located to one side of the sensitive axis 67 of the low frequency accelerometer with its sensitive axis parallel thereto. A second high frequency accelerometer 68 is located an equal distance to the other side of the axis 67 and aligned therewith. the signals from the two high frequency accelerometers are combined in summing means 69 to find an average linear acceleration value. The high frequency accelerometer pair has an effective centre of percussion in respect of acceleration forces including linear and rotational components coincident with the centre of mass of the proof mass 61.

Thus both the low frequency accelerometer and high frequency accelerometer pair effectively experience the acceleration acting at the same point and eliminates errors due to physical separation.

The high frequency accelerometer or accelerometers of a pair may be other than the capacitive piezo electric type described herein, such as piezo resistive, but are preferably miniature types to provide maximum scope for locating them in relation to the low frequency accelerometer.

Similarly the low frequency accelerometer may be a force feedback instrument other than the pendulous type described herein, the ability to mitigate vibropendulous errors being redundant but retaining the ability to tailor the feedback loop response to satisfy any particular criteria of the instrument. Whether a single axis accelerometer system in accordance with the present invention includes a single high frequency accelerometer as shown in FIG. 2 or a pair as shown in FIG. 3 there is considerable freedom in mounting the high frequency accelerometers in the system so that when a plurality of systems are employed, for example in a three axis combination, a more efficient arrangement may be obtained.

This is most readily appreciated by example in which the accelerometer system of FIG. 2 is employed in an inertial platform arrangement. Such arrangements are well known and the principal components are illustrated schematically in FIG. 4 which together with FIG. 2 shows three single-axis accelerometer systems 30', 30" and 30''' carried by and having sensitive axes aligned in the orthogonal X, Y and Z axes of the inertial platform. The platform also carries three single-axis gyros 70', 70" and 70''' each also aligned to measure rotational forces with respect to the orthogonal X, Y and Z axes. The outputs of accelerometers and gyros are fed to a computer shown generally at 71 which uses standard techniques to compute the spatial position of the platform and does not require further description. The computer is also organised to take into account the receipt of the accelerometer signals in the higher frequency vibration band and from them to use algorithms based on standard error correction equations to compute and apply low-frequency corrections to the low-frequency accelerometer signals of other axes.

Referring now to FIG. 5, an inertial platform is indicated schematically comprising a cluster 80 formed by the three accelerometer systems 30', 30" and 30''' carried on the inner walls of a cube structure and the three gyro packages 70', 70" and 70''' attached to the exterior walls of the structure. The gyros are compact laser gyros and mechanically dithered to effect operation. They are also operated in the strapdown mode, that is, the platform is not suspended to maintain orientation in space by movement with respect to a vehicle carrying the platform, but is constrained to move with the vehicle being susceptible both to vibrations transmitted from the vehicle and those generated by operation of the gyros.

The accelerometer systems 30', 30" and 30''' are constructed such that the high-frequency accelerometer 46 is displaced from the main bulk of the low-frequency accelerometer 10' etc. enabling all three accelerometer systems to be located so that the low-frequency accelerometers are mounted with their centers of percussion close to the centre of gravity of the platform and the high-frequency accelerometers are substantially coexistant in space.

It will be appreciated that a similar platform may be constructed employing single axis accelerometer systems as shown in FIG. 3, the high frequency accelerometers being disposed in each single axis accelerometer system such that the centres of percussion of all three pairs are coexistant even though the accelerometers themselves are separated. With the particular construction of single axis accelerometers of FIG. 3, in addition to the sum of the two high frequency accelerometer signals providing the along-axis acceleration component through the common centre of percussion, the difference between the two high frequency accelerometer signals may be taken as a measure of rotation of the accelerometer means about an orthogonal axis. Thus the three orthogonally disposed accelerometer means are able to provide the rotational measurements normally provided by the gyros and enabling the error corrections to be more conveniently made.

The use of a single-axis accelerometer system in accordance with the first aspect of the present invention thus enables construction of an inertial platform of improved performance.

Clearly other forms of platform may employ such single-axis accelerometer systems which systems may also be employed in any arrangement in which a wider operating bandwidth is required and potential scale factor errors through the use of more than one accelerometer are to be avoided.

We claim:

1. A single axis accelerometer system comprising
   (i) a low frequency accelerometer of the force feedback type including an inertial proof mass mounted to be displaced from a datum position along a sensitive axis by an acceleration force, a displacement transducer operable to produce a feedback signal as a function of displacement of the proof mass from the datum position and capture means responsive to a capture current flowing therein to produce a restoring force on the proof mass to balance the acceleration force, said capture current being provided as a function of the feedback signal,
   (ii) a high frequency accelerometer fixed in relation to the low frequency accelerometer and responsive to high frequency vibrations along said sensitive axis to produce an acceleration related signal, and
   (iii) signal processing means operable to mix the feedback signal from the proof mass displacement transducer and acceleration related signal produced by the high frequency accelerometer and derive therefrom the capture current.

2. A single axis accelerometer as claimed in claim 1 in which the signal processing means includes signal shaping means operable to vary at least one of the signals to be mixed in accordance with a predetermined transfer function.

3. A single axis accelerometer as claimed in claim 2 in which the signal shaping means comprises a filter network operable to pass acceleration related signals provided by the high frequency accelerometer within a predetermined band of frequencies.

4. A single axis accelerometer as claimed in claim 3 in which the signal shaping means comprises a signal shaping network operable to form an integral component of the feedback signal from the proof mass displacement transducer.

5. A single axis acceleometer as claimed in claim 4 including a further high frequency accelerometer (as herein defined) fixed in relation to the low frequency accelerometer with the directions of the sensitive axes of the high frequency accelerometers extending parallel to the sensitive axis of the low frequency accelerometer and disposed equidistantly at each side thereof, and combining means operable to provide an output signal representing the average acceleration signal from the two high frequency accelerometers.

6. A single axis acceleometer as claimed in claim 3 including a further high frequency accelerometer (as herein defined) fixed in relation to the low frequency accelerometer with the directions of the sensitive axes of the high frequency accelerometers extending parallel to the sensitive axis of the low frequency accelerometer and disposed equidistantly at each side thereof, and combining means operable to provide an output signal representing the average acceleration signal from the two high frequency accelerometers.

7. A single axis accelerometer as claimed in claim 2 including a further high frequency accelerometer (as herein defined) fixed in relation to the low frequency accelerometer with the directions of the sensitive axes of the high frequency accelerometers extending parallel to the sensitive axis of the low frequency accelerometer and disposed equidistantly at each side thereof, and combining means operable to provide an output signal representing the average acceleration signal from the two high frequency accelerometers.

8. A single axis acceleometer as claimed in claim 1 including a further high frequency accelerometer fixed in relation to the low frequency accelerometer with the directions of the sensitive axis of the high frequency accelerometers extending parallel to the sensitive axis of the low frequency accelerometer and disposed equidistantly at each side thereof, and combining means operable to provide an output signal representing the average acceleration signal from the two high frequency accelerometers.

9. An inertial platform arrangement including three single-axis accelerometer systems as claimed in claim 1 arranged with their sensitive axes mutually orthogonal.

10. An inertial platform arrangement as claimed in claim 9 in which the single-axis accelerometer systems are disposed with the centres of percussion of the high-frequency accelerometers substantially co-existant.

* * * * *